(12) United States Patent
Morschhäuser et al.

(10) Patent No.: US 6,833,419 B2
(45) Date of Patent: Dec. 21, 2004

(54) FLUORINE-MODIFIED COMB POLYMERS BASED ON ACRYLOYDIMETHYLTAURINE ACID

(75) Inventors: Roman Morschhäuser, Mainz (DE); Christoph Kayser, Mainz (DE); Matthias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/433,120

(22) PCT Filed: Nov. 28, 2001

(86) PCT No.: PCT/EP01/13864

§ 371 (c)(1), (2), (4) Date: Nov. 24, 2003

(87) PCT Pub. No.: WO02/44227

PCT Pub. Date: Jun. 6, 2002

(65) Prior Publication Data

US 2004/0116634 A1 Jun. 17, 2004

(30) Foreign Application Priority Data

Dec. 1, 2000 (DE) .......................................... 10059833

(51) Int. Cl.⁷ ................................................ C08F 28/02
(52) U.S. Cl. ........................ 526/288; 526/277; 526/250; 526/303.1; 526/307.1; 526/307.2
(58) Field of Search ..................... 526/307.2, 307.1, 526/287, 303.1, 288, 250

(56) References Cited

U.S. PATENT DOCUMENTS

| | | | |
|---|---|---|---|
| 5,275,809 A | 1/1994 | Chen et al. .................... 424/70 |
| 5,379,841 A | 1/1995 | Pusch et al. ................. 166/295 |
| 6,120,780 A | 9/2000 | Dupuis et al. ............... 424/401 |
| 6,355,752 B1 * | 3/2002 | Brungs et al. ............... 526/287 |
| 6,380,137 B1 | 4/2002 | Heier et al. .................. 507/121 |
| 6,395,853 B1 | 5/2002 | Oswald et al. ........... 526/307.2 |
| 6,437,068 B2 * | 8/2002 | Loffler et al. ................ 526/264 |
| 6,448,297 B1 * | 9/2002 | Turowski-Wanke et al. .. 516/56 |
| 6,489,395 B2 * | 12/2002 | Loffler ......................... 524/845 |
| 6,645,476 B1 * | 11/2003 | Morschhauser et al. ... 424/70.1 |
| 2002/0082373 A1 | 6/2002 | Brungs et al. ............... 526/287 |

FOREIGN PATENT DOCUMENTS

| | | |
|---|---|---|
| EP | 0 522 756 | 1/1993 |
| EP | 0 816 403 | 1/1998 |
| EP | 1 028 129 | 8/2000 |
| EP | 1 059 316 | 12/2000 |
| EP | 1 069 142 | 1/2001 |
| WO | WO 98/00094 | 1/1998 |

* cited by examiner

*Primary Examiner*—Tatayana Zalukaeva
(74) *Attorney, Agent, or Firm*—Richard P. Silverman

(57) ABSTRACT

The invention provides water-soluble or water-swellable copolymers obtained by free-radical copolymerization of A) acryloyldimethyltaurine and/or acryloyldimethyltaurates, B) optionally, one or more other olefinically unsaturated, optionally crosslinking, comonomers containing at least one oxygen, nitrogen, sulfur or phosphorus atom and possessing a molecular weight of less than 500 g/mol, and C) one or more at least monofunctional, fluorine-containing components capable of free-radical polymerization, the copolymerization D) taking place in the presence or absence of at least one polymeric additive having number-average molecular weights of from 200 g/mol to $10^9$ g/mol.

The water-soluble or water-swellable copolymers of the present invention are useful in paper processing, laundry detergents, textile processing, petroleum extraction and formulating cosmetics.

12 Claims, No Drawings

FLUORINE-MODIFIED COMB POLYMERS BASED ON ACRYLOYDIMETHYLTAURINE ACID

The present invention relates to fluorine-modified comb polymers based on acryloyldimethyltaurine.

In recent years water-soluble polymers have acquired a continually increasing importance in industry and science. In volume terms, polyelectrolytes are occupying a very large proportion of the overall annual production. They find application, for example, in paper processing, in the laundry detergents industry, in textile processing, in petroleum extraction or as important base materials for cosmetics. In the cosmetics sector a supporting role is played by polyelectrolytes. Besides water-soluble surface-active substances there is a high demand in this sector for systems which thicken oil and water. Thickeners of this kind, particularly the "superabsorbents" prepared on the basis of polyacrylic acid, have progressed since their development in the 1970s to become a pillar of the hygiene sector. In their crosslinked versions, partly or fully neutralized polyacrylic acids and their water-soluble copolymers are employed in numerous cosmetic formulations as bodying agents. The diversity of possible structures and the diverse possible applications associated therewith are manifested not least in a host of patents filed worldwide since the mid-1970s. In the 1990s, innovative thickeners based on 2-acrylamido-2-methyl-1-propanesulfonic acid (AMPS) and their salts were introduced into the market (EP 816 403 and WO 98/00094). In both homopolymer and copolymer form (®Aristoflex AVC, Clariant GmbH) such thickeners are superior in many respects to the corresponding polycarboxylates (Carbopols). For example, thickener systems based on AMPS display outstanding properties in pH ranges below pH 6, i.e., in a pH range in which it is no longer possible to operate with conventional polycarboxylate thickeners. Moreover, the microgel structure of such thickeners leads to a particularly pleasant skin sensation. The ease of processing and the favorable toxicological profile of the principal monomer imbue these thickeners with a high application potential.

Over recent years representatives of a new thickener design have entered the market. In these thickeners two different properties have been combined in one polymer, thereby opening up new fields of application. Thickening emulsifiers or dispersants are but two examples of this new class of substance. Brand names that may be mentioned include the Pemulens® TR-1 and TR-2 from BF Goodrich or the Aculyn® products from Rohm & Haas. All existing versions are based on hydrophobically modified versions of the conventional polyacrylates.

Comparable polymers which develop hydrophobic interactions and hence physical crosslinking through fluorine-containing groups were hitherto unknown. Some fluorotelomers which possess one or a maximum of two fluorine-containing groups per polymer chain are available.

Through free-radical copolymerization of acryloyldimethyltaurine (AMPS) and/or its salts with suitable vinylically monofunctional or polyfunctional fluorine derivatives, in the presence where appropriate of comonomers and polymeric additives, it was possible to synthesize both crosslinked and noncrosslinked structures having highly advantageous performance properties.

The invention provides water-soluble or water-swellable copolymers preparable by free-radical copolymerization of:
A) acryloyldimethyltaurine and/or acryloyldimethyltaurates,
B) if desired, one or more other olefinically unsaturated, optionally crosslinking, comonomers containing at least one oxygen, nitrogen, sulfur or phosphorus atom and possessing a molecular weight of less than 500 g/mol, and
C) one or more at least monofunctional, fluorine-containing components capable of free-radical polymerization, the copolymerization
D) taking place in the presence or absence of at least one polymeric additive having number-average molecular weights of from 200 g/mol to $10^9$ g/mol.

The copolymers of the invention preferably possess a molecular weight of from $10^3$ g/mol to $10^9$ g/mol, more preferably from $10^4$ to $10^7$ g/mol, very preferably from $5*10^4$ to $5*10^6$ g/mol.

The acryloyldimethyltaurates can be the organic or inorganic salts of acryloyl-dimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be ($C_1$–$C_{22}$)-alkyl radicals or ($C_2$–$C_{10}$)-hydroxyalkyl radicals. Preference is also given to mono- to triethoxylated ammonium compounds with a different degree of ethoxylation. It should be noted that the invention also embraces mixtures of two or more of the abovementioned representatives.

The degree of neutralization of the acryloyldimethyltaurine can be between 0 and 100%, particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 22. Particularly preferred unsaturated carboxylic acids are acrylic acid, methacrylic acid, styrenesulfonic acid, maleic acid, fumaric acid, crotonic acid, itaconic acid, and senecic acid. Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another are ($C_1$–$C_{22}$)-alkyl radicals or ($C_2$–$C_{10}$)-hydroxyalkyl radicals. It is additionally possible to employ mono- to triethoxylated ammonium compounds with a different degree of ethoxylation. The degree of neutralization of the carboxylic acids can be between 0 and 100%. Further preferred comonomers are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide; hydroxyethylmethacrylamide, hydroxypropylmethacrylamide, and mono[2-(methacryloyloxy)ethyl] succinate; N,N-dimethylamino methacrylate; diethylaminomethyl methacrylate;

acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene. Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable polymerizable fluorine-containing components C) include all compounds which are olefinically at least monounsaturated and which are capable of free-radical copolymerization with acryloyldimethyltaurine and/or acryloyldimethyl-taurates—and optionally further comonomers—under the reaction conditions chosen in each case. The distribution of the individual fluorine-containing monomers across the polymer chains which form need not necessarily be random. The invention also embraces the formation of blocklike (including multiblock) or gradient-like structures, for example. Combinations of two or more different fluorine-containing components C) are also possible, it being clear to the expert that monofunctional representatives lead to the formation of comb-shaped structures while di-, tri-, or polyfunctional components C) lead to structures which are at least partly crosslinked.

Preferred fluorine-containing components C) are those of formula (I).

$$R^1-Y-(CH_2)_r(CF_2)_sCF_3 \qquad (I)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical. The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —($C_1$ to $C_{50}$)alkyl-O—, -phenyl-O—, -benzyl-O—, —($C_5$ to $C_8$)cycloalkyl-O—, —($C_1$-$C_{50}$)alkenyl-O—, —(CH($CH_3$)—$CH_2$—O)$_n$—, —O—($CH_2$—$CH_2$—O)$_n$—, and —([CH($CH_3$)—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another can be numbers between 0 and 200.

Particularly preferred fluorine-containing components C) are perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether] acrylate, perfluoroctylethanolyl poly[ethylglycol-block-co-propylene glycol ether] methacrylate and/or perfluoroctylpropanolyl polypropylene glycol ether methacrylate.

Based on the total mass of the copolymers the weight fraction of the comonomers C) can be from 0.1 to 99.9% by weight, preferably from 0.1 to 50% by weight, more preferably from 0.2 to 30% by weight, and very preferably from 0.5 to 20% by weight.

In one preferred embodiment the copolymerization is conducted in the presence of at least one polymeric additive D), the additive D) being added wholly or partly in solution to the polymerization medium before the actual copolymerization. The use of two or more additives D) is likewise in accordance with the invention. Crosslinked additives D) may likewise be used. The additives D) or mixtures thereof must only be wholly or partly soluble in the chosen polymerization medium. During the actual polymerization step the additive D) has a number of functions. On the one hand it prevents the formation of overcrosslinked polymer fractions in the copolymer which forms in the actual polymerization step, and on the other hand the additive D) is statistically attacked by active free radicals in accordance with the very well-known mechanism of graft copolymerization. Depending on the particular additive D), this results in greater or lesser fractions of the additive being incorporated into the copolymers. Moreover, suitable additives D) possess the property of altering the solution parameters of the copolymers which form during the free-radical polymerization reaction in such a way that the average molecular weights are shifted to higher values. As compared with analogous copolymers prepared without the addition of the additives D), those prepared with the addition of additives D) advantageously exhibit a significantly higher viscosity in aqueous solution.

Preferred additives D) are homopolymers and copolymers which are soluble in water and/or alcohols. The term "copolymers" also comprehends those having more than two different monomer types. Particularly preferred additives D) are homopolymers and copolymers of N-vinylformamide, N-vinylacetamide, N-vinylpyrrolidone, ethylene oxide, propylene oxide, acryloyldimethyltaurine, N-vinylcaprolactone, N-vinylmethylacetamide, acrylamide, acrylic acid, methacrylic acid, N-vinylmorpholide, hydroxyethyl methacrylate, diallyidimethylammonium chloride (DADMAC) and/or [2-(methacryloyloxy)ethyl] trimethylammonium chloride (MAPTAC); polyalkylene glycols and/or alkylpolyglycols.

Particularly preferred additives D) are polyvinylpyrrolidones (e.g., K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives D) is preferably from $10^2$ to $10^7$ g/mol, more preferably from $0.5*10^4$ to $10^6$ g/mol.

The amount in which the polymeric additive D) is used, based on the total mass of the monomers to be polymerized during the copolymerization, is preferably from 0.1 to 90% by weight, more preferably from 1 to 20% by weight, and with particular preference from 1.5 to 10% by weight.

In one further preferred embodiment the copolymers of the invention are crosslinked, i.e., they contain comonomers containing at least two polymerizable vinyl groups. Preferred crosslinkers are methylenebisacrylamide; methylenebismethacrylamide; esters of unsaturated monocarboxylic and polycarboxylic acids with polyols, preferably di-acrylates and tri-acrylates and -methacrylates, more preferably butanediol and ethylene glycol diacrylate and -methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA).

The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures and emulsions of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide (DLP) or azo initiators, such as azodiisobutyronitrile (AIBN) and azobisamidopropyl hydrochloride (ABAH), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

The polymerization reaction is advantageously conducted, for example, as a precipitation polymerization, emulsion polymerization, solution polymerization, bulk polymerization, or gel polymerization. Particularly advantageous for the profile of properties of the copolymers of the invention is precipitation polymerization, preferably in tert-butanol. The copolymers of the invention are very suitable for stabilizing and thickening fluorine-containing aqueous systems. By fluorine-containing aqueous systems are meant for example mixtures of water with fluoroalcohols, fluorosurfactants or fluoroalkanes. A particular possibility is that of stabilizing fluorine-containing emulsions with very high fractions of fluoroalkyl compounds, perfluoroalkylethanols, perfluoroalkylpropanols, and fluorosurfactants (>30%). The copolymers are also extremely suitable for stabilizing combination formulations, containing for example fats or oils, including silicone oils, in combination with fluorine-containing compounds. In the case of the copolymers the fluorine content can be varied virtually as desired, resulting in a broad property spectrum. A further advantage of the copolymers is that the aggregation-capable hydrophobic fluorine-containing group is at the same time also lipophobic, resulting in the attractive hydrophobic interactions occurring exclusively between the fluorine-containing groups. As a consequence, in an aqueous solution or a hydrogel, for example, lipophilic groups or molecules do not enter into interaction with the fluorine-containing groups of the polymers. Accordingly, in a system containing water and oil, for example, it is possible to influence specifically the consistency of the aqueous phase without affecting the viscosity of the oil phase. This is of advantage if, for example, a phase separation is desired. Also conceivable, therefore, are applications in electrical engineering or electrophoresis. The polymers of the invention may likewise be used to mediate attractive interactions between fluorinated surfaces and hydrophilic boundary media. This property is of interest, for example, for the construction of selective membranes. It is likewise possible to effect compatibilization, dispersion or wetting of fluorine-containing polymers or polymer particles. Hydrophilic surfaces, such as ceramic, minerals, glass, metal or else fabrics and leather, can be hydrophobized, for example, by the polymers of the invention. In the cosmetics sector the copolymers can be used, for example, to formulate a very wide variety of W/O emulsions and O/W emulsions. Examples are skin protection formulations, shampoos, rinses, lotions, treatments, decorative cosmetics, makeup, powders, deosticks, antiperspirants, shower baths, liquid soap, bar soap, cleansing milk, sun protection formulations, hair colorants, hair gels, and hair sprays, to name but a few. An advantageous feature in the case of cosmetic applications is that the copolymers impart a pleasant skin feel to the compositions. In the case of applications in the hair cosmetology sector the copolymers exhibit a pleasant conditioning effect of the polymers and give the hair good combability and shine.

The following examples are intended to illustrate the invention without, however, restricting it thereto.

EXAMPLE 1

| Reactants | amount (g) |
| --- | --- |
| NH$_3$-neutralized AMPS | 80 |
| ® Perfluoroctylpropylol methacrylate | 10 |
| t-Butanol | 400 |
| DLP (initiator) | 1 |
| Poly-N-vinylpyrrolidone (® K-15BASF) | 5 |

The polymer was prepared by the precipitation method in tert-butanol. The reactants in t-butanol were introduced as an initial charge and the reaction mixture was rendered inert, and then, after initial heating, the reaction was initiated by addition of dilauroyl peroxide (DLP). The polymer was isolated by removal of the solvent under suction and by subsequent vacuum drying. In 1% aqueous solution the polymer exhibits a viscosity of 45 000 mPas, with a slightly opalescent appearance. The skin feel of the gel was markedly superior to that of fluorine-free versions.

EXAMPLE 2

| Reactants | amount (g) |
|---|---|
| NH₃-neutralized AMPS | 70 |
| N-Vinylpyrrolidone | 5 |
| Perfluoroctylethyloxyglyceryl methacrylate | 8 |
| Isopropanol | 500 |
| AIBN (initiator) | 1 |

The polymer was prepared by the solution polymerization method in isopropanol. The monomers were dissolved in the corresponding alcohol, the reaction mixture was rendered inert, and then, after initial heating, the reaction was initiated by addition of diazoisobutyronitrile (AIBN). The polymer solution was subsequently concentrated and the polymer was isolated by vacuum drying.

EXAMPLE 3

| Reactants | amount (g) |
|---|---|
| AMPS | 80 |
| Perfluoroctylpolyethylene glycol methacrylate | 20 |
| Cyclohexane | 200 |
| Water | 300 |
| ® Span 80 | 1 |
| Na₂S₂O₈ (initiator) | 1 |

The polymer was prepared by the emulsion method in water. The monomers were emulsified in a water/cyclohexane mixture using ®Span 80, the reaction mixture was rendered inert using N₂, and then, after initial heating, the reaction was initiated by addition of sodium peroxodisulfate. The polymer emulsion was subsequently evaporated down (cyclohexane acting as azeotrope former for water) and by this means the polymer was isolated.

EXAMPLE 4

| Reactants | amount (g) |
|---|---|
| NH₃-neutralized AMPS | 80 |
| Perfluorohexylpolyethylene glycol methacrylate | 20 |
| t-Butanol | 300 |
| DLP (initiator) | 1 |

This polymer was prepared by the precipitation method in tert-butanol. The monomers in t-butanol were introduced as an initial charge, the reaction mixture was rendered inert, and then, after initial heating, the reaction was initiated by addition of (dilauroyl peroxide) DLP. The polymer was isolated by removal of the solvent under suction and subsequent vacuum drying. In 1% solution in distilled water the polymer exhibits a clear appearance with a viscosity of 35 000 mPas. In comparison therewith the fluorine-free version, with the same composition, showed a similar appearance and a viscosity of 12 000 mPas under identical measurement conditions. The skin feel of the fluorine-containing monomer was significantly improved over that of the comparison standards.

EXAMPLE 5

| Reactants | amount (g) |
|---|---|
| Na-neutralized AMPS | 50 |
| Perfluoroctylethyloxyglyceryl methacrylate | 45 |
| t-Butanol | 300 |
| Trimethylolpropane triacrylate (TMPTA) | 1.8 |
| ABAH | 1 |
| Poly[N-vinylformamide] | 8 |

The polymer was prepared by the precipitation method in tert-butanol. The monomers in t-butanol were introduced as an initial charge, the reaction mixture was rendered inert, and then, after initial heating, the reaction was initiated by addition of azobisamidopropyl hydrochloride (ABAH). The polymer was isolated by removal of the solvent under suction and by subsequent vacuum drying.

What is claimed is:

1. A water-soluble or water-swellable copolymer obtained by free-radical copolymerization of
    A) acryloyldimethyltaurine and/or acryloyldimethyltaurates,
    B) optionally, one or more other olefinically unsaturated, optionally crosslinking, comonomers containing at least one oxygen, nitrogen, sulfur or phosphorus atom and possessing a molecular weight of less than 500 g/mol, and
    C) one or more at least monofunctional, fluorine-containing components capable of free-radical polymerization, at least one fluorine-containing component being a compound of the formula (I)

$$R^1\text{—}Y\text{—}C_rH_{2r}C_sF_{2s}CF_3 \qquad (I)$$

where
    $R^1$ is an acryloyl or methacryloyl radical;
    Y is a chemical bridge, and
    r and s are stoichiometric coefficients which independently of one another can be numbers between 0 and 200,
    and with the copolymerization taking place
    D) optionally in the presence or absence of at least one polymeric additive having number-average molecular weight of from 200 g/mol to $10^9$ g/mol.

2. The water-soluble or water-swellable copolymer of claim 1, wherein the fluorine-containing component C) is selected from the group consisting of perfluorohexylethanol methacrylate,
    perfluorohexoylpropanol methacrylate
    perfluoroctylethanol methacrylate,
    perfluoroctylpropanol methacrylate,
    perfluorohexylethanolyl polyglycol ether methacrylate,
    perfluorohexoylpropanolyl poly[ethylglycol-co-propylene glycol ether] acrylate,
    perfluoroctylethanolyl poly[ethylglycol-block-co-propylene glycol ether] methacrylate,
    perfluoroctylpropanolyl polypropylene glycol ether methacrylate, and mixtures thereof.

3. The water-soluble or water-swellable copolymer of claim 1, further comprising one or more comonomer B).

4. The water-soluble or water-swellable copolymer as claimed in claim 3, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, or methallylsulfonic acid or the esters or salts thereof, and mixtures thereof.

5. The water-soluble or water-swellable copolymer of claim 1, wherein the copolymerization takes place in the presence of at least one polymeric additive D).

6. The water-soluble or water-swellable copolymer as claimed in claim 5, wherein the polymeric additive D) is selected from the group consisting of polyalkylene glycol, alkylpolyglycol and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC) and/or [2-(methacryloyloxy)ethyl] trimethylammonium chloride (MAPTAC), and mixtures thereof.

7. The water-soluble or water-swellable copolymer as claimed in claim 6, wherein the polymeric additive D) is selected from the group consisting of poly(N-vinylformamides), poly(N-vinylcaprolactams), and copolymers of a compound selected from the group consisting of N-vinylpyrrolidone, N-vinylformamide, acrylic acid, and mixtures thereof.

8. The water-soluble or water-swellable copolymer of claim 1, wherein the copolymer is crosslinked.

9. The water-soluble or water-swellable copolymer of claim 1, wherein the copolymer is prepared by precipitation polymerization in tert-butanol.

10. The water-soluble or water-swellable copolymer of claim 1, wherein the chemical bridge Y is selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$-C$_{50}$)alkyl-O—, —O-phenyl-O—, —O-benzyl-O—, —O—(C$_5$-C$_8$)cycloalkyl-O—, —O—(C$_1$-C$_{50}$)alkenyl-O—, —O—(CH(CH$_3$)—CH$_2$—O)$_n$—, —O—(CH$_2$—CH$_2$—O)$_n$—, —O—([CH—CH$_2$—O]$_n$—[CH$_2$—CH$_2$—O]$_m$)$_o$—, and mixtures thereof, where n, m, and o independently of one another denote numbers from 0 to 200.

11. A water-soluble or water-swellable copolymer obtained by free-radical copolymerization of acryloyldimethyltaurine and/or acryloyldimethyltaurate, with one or more at least monofunctional, fluorine-containing component capable of free-radical polymerization, at least one fluorine-containing component being a compound of the formula (I)

$$R^1—Y—C_rH_{2r}C_sF_{2s}CF_3 \qquad (I)$$

wherein $R^1$ is an acryloyl or methacryloyl radical;

Y is a radical selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$-C$_{50}$)alkyl-O—, —O-phenyl-O—, —O-benzyl-O—, —O—(C$_5$-C$_8$)cycloalkyl-O—, —O—(C$_1$-C$_{50}$)alkenyl-O—, —O—(CH(CH$_3$)—CH$_2$—O)$_n$—, —O—(CH$_2$—CH$_2$—O)$_n$—, —O—([CH—CH$_2$—O]$_n$—[CH$_2$—CH$_2$—O]$_m$)$_o$—, and mixtures thereof where n, m, and o independently of one another denote numbers between 0 and 200, and r and s are stoichiometric coefficients which independently of one another can be numbers between 0 and 200.

12. The water-soluble or water-swellable copolymer of claim 11, said copolymerization further comprising being with or in the presence of at least one of component selected from the group consisting of a) one or more olefinically unsaturated comonomers containing at least one oxygen, nitrogen, sulfur or phosphorous atom and having a molecular weight of less than 500 g/mol, b) at least one polymeric additive having number-average molecular weight of from 200 g/mol to $10^9$ g/mol, and mixtures thereof.

* * * * *